(12) United States Patent
Harms et al.

(10) Patent No.: US 10,398,845 B2
(45) Date of Patent: Sep. 3, 2019

(54) DRUG DELIVERY DEVICE

(71) Applicant: SANOFI-AVENTIS DEUTSCHLAND GMBH, Frankfurt am Main (DE)

(72) Inventors: Michael Harms, Frankfurt am Main (DE); Volker Korger, Frankfurt am Main (DE); Uwe Dasbach, Frankfurt am Main (DE); Steffen Raab, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 0 days.

(21) Appl. No.: 15/805,924

(22) Filed: Nov. 7, 2017

(65) Prior Publication Data

US 2018/0056008 A1    Mar. 1, 2018

Related U.S. Application Data

(63) Continuation of application No. 15/352,904, filed on Nov. 16, 2016, now Pat. No. 9,839,751, which is a
(Continued)

(30) Foreign Application Priority Data

Mar. 31, 2009  (EP) .................................... 09004666

(51) Int. Cl.
*A61M 5/24*     (2006.01)
*A61M 5/315*    (2006.01)

(52) U.S. Cl.
CPC .......... *A61M 5/31543* (2013.01); *A61M 5/24* (2013.01); *A61M 5/31525* (2013.01); *A61M 5/31528* (2013.01); *A61M 2005/2481* (2013.01)

(58) Field of Classification Search
CPC ................ A61M 5/31543; A61M 5/24; A61M 5/31525; A61M 5/31528; A61M 2005/2481

See application file for complete search history.

(56) References Cited

U.S. PATENT DOCUMENTS

| | | |
|---|---|---|
| 533,575 A | 2/1895 | Wilkens |
| 4,367,739 A | 1/1983 | LeVeen et al. |

(Continued)

FOREIGN PATENT DOCUMENTS

| | | |
|---|---|---|
| CA | 2138528 C | 12/1998 |
| CA | 2359375 A1 | 7/2000 |

(Continued)

OTHER PUBLICATIONS

"Pen-injectors for medical use—Part 1: Pen-injectors—Requirements and test methods," International Standard, reference No. ISO 11608-1:2000(E), first edition Dec. 15, 2000, 32 pages.
(Continued)

*Primary Examiner* — Lauren P Farrar
(74) *Attorney, Agent, or Firm* — Fish & Richardson P.C.

(57) ABSTRACT

A mechanism in the body is used to drive a piston rod and comprises means for guiding the movement of the piston rod relatively to the body while delivering the drug. Further means are provided for releasing the piston rod from the means for guiding the movement, thus enabling a reset of the piston rod to a start position, especially after the receptacle has been emptied and is to be refilled. The device is constructed in such a manner that a reset of the piston rod is facilitated.

8 Claims, 4 Drawing Sheets

Related U.S. Application Data continuation of application No. 13/258,160, filed as application No. PCT/EP2010/054343 on Mar. 31, 2010, now Pat. No. 9,526,840.

(60) Provisional application No. 61/169,858, filed on Apr. 16, 2009.

(56) References Cited

U.S. PATENT DOCUMENTS

| | | | |
|---|---|---|---|
| 4,744,790 A * | 5/1988 | Jankowski | A61M 5/24 604/232 |
| 4,865,591 A | 9/1989 | Sams | |
| 5,092,842 A | 3/1992 | Bechtold et al. | |
| 5,226,895 A | 7/1993 | Harris | |
| 5,226,896 A | 7/1993 | Harris | |
| 5,279,586 A | 1/1994 | Balkwill | |
| 5,304,152 A | 4/1994 | Sams | |
| 5,320,609 A | 6/1994 | Haber et al. | |
| 5,378,233 A | 1/1995 | Haber et al. | |
| 5,383,865 A | 1/1995 | Michel | |
| 5,391,157 A | 2/1995 | Harris et al. | |
| 5,480,387 A | 1/1996 | Gabriel et al. | |
| 5,505,704 A | 4/1996 | Pawelka et al. | |
| 5,582,598 A | 12/1996 | Chanoch | |
| 5,626,566 A | 5/1997 | Petersen et al. | |
| 5,674,204 A | 10/1997 | Chanoch | |
| 5,688,251 A | 11/1997 | Chanoch | |
| 5,807,346 A | 9/1998 | Frezza | |
| 5,820,602 A | 10/1998 | Kovelman et al. | |
| 5,851,079 A | 12/1998 | Horstman et al. | |
| 5,921,966 A | 7/1999 | Bendek et al. | |
| 5,957,896 A | 9/1999 | Bendek et al. | |
| 5,961,495 A | 10/1999 | Walters et al. | |
| 6,004,297 A | 12/1999 | Steenfeldt-Jensen et al. | |
| 6,193,698 B1 | 2/2001 | Kirchhofer et al. | |
| 6,221,046 B1 | 4/2001 | Burroughs et al. | |
| 6,235,004 B1 | 5/2001 | Steenfeldt-Jensen et al. | |
| 6,248,095 B1 | 6/2001 | Giambattista et al. | |
| 6,562,006 B1 | 5/2003 | Hjertman et al. | |
| 6,613,023 B2 | 9/2003 | Kirchhofer et al. | |
| 6,699,224 B2 | 3/2004 | Kirchhofer et al. | |
| 6,899,698 B2 | 5/2005 | Sams | |
| 6,932,794 B2 | 8/2005 | Giambattista et al. | |
| 6,936,032 B1 | 8/2005 | Bush, Jr. et al. | |
| 7,169,132 B2 | 1/2007 | Bendek et al. | |
| 7,241,278 B2 | 7/2007 | Moller | |
| 7,500,966 B2 | 3/2009 | Hommann | |
| 7,678,084 B2 | 3/2010 | Judson et al. | |
| 7,850,662 B2 | 12/2010 | Veasey et al. | |
| 8,187,233 B2 | 5/2012 | Harms et al. | |
| 2002/0052578 A1 | 5/2002 | Moller | |
| 2002/0120235 A1 | 8/2002 | Enggaard | |
| 2003/0050609 A1 | 3/2003 | Sams | |
| 2004/0059299 A1 | 3/2004 | Moller | |
| 2004/0097883 A1 * | 5/2004 | Roe | A61M 5/31541 604/207 |
| 2004/0210199 A1 * | 10/2004 | Atterbury | A61M 5/31535 604/224 |
| 2004/0267207 A1 | 12/2004 | Veasey et al. | |
| 2005/0113765 A1 | 5/2005 | Veasey et al. | |
| 2005/0137534 A1 | 6/2005 | Hommann | |
| 2006/0153693 A1 | 7/2006 | Fiechter et al. | |
| 2007/0016143 A1 | 1/2007 | Miller et al. | |
| 2007/0093761 A1 | 4/2007 | Veasey et al. | |
| 2008/0171997 A1 | 7/2008 | Kohlbrenner et al. | |
| 2008/0306446 A1 | 12/2008 | Markussen | |
| 2009/0275916 A1 | 11/2009 | Harms et al. | |

FOREIGN PATENT DOCUMENTS

| | | |
|---|---|---|
| EP | 0496141 A1 | 7/1992 |
| EP | 0897729 A2 | 2/1999 |
| EP | 0937471 | 8/1999 |
| EP | 0937476 | 8/1999 |
| EP | 1776975 A2 | 4/2007 |
| EP | 1923083 | 5/2008 |
| WO | 93/07922 A1 | 4/1993 |
| WO | 93/24160 A1 | 12/1993 |
| WO | 94/22507 | 10/1994 |
| WO | 99/38554 | 8/1999 |
| WO | 01/10484 | 2/2001 |
| WO | 02/30495 A2 | 4/2002 |
| WO | 02/092153 | 11/2002 |
| WO | 02/092153 A2 | 11/2002 |
| WO | 03/080160 A1 | 10/2003 |
| WO | 2006/084876 A1 | 8/2006 |
| WO | 2008/074897 | 6/2008 |

OTHER PUBLICATIONS

European Search Report for EP Patent Application No. 09004666, dated Aug. 19, 2009.

International Search Report for PCT Patent Application No. PCT/EP2010/054343, dated Jul. 13, 2010.

International Preliminary Report on Patentability for International App. No. PCT/EP2010/054343, dated Oct. 4, 2011.

* cited by examiner

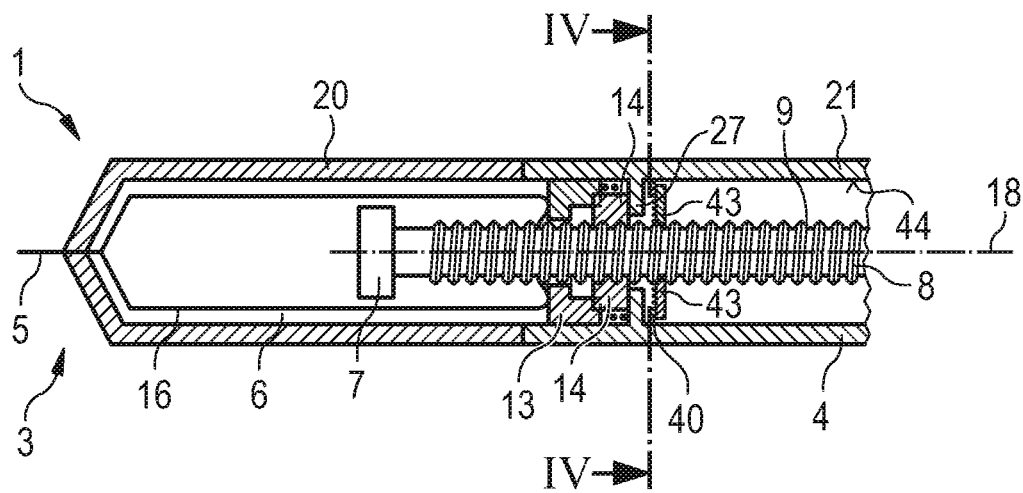
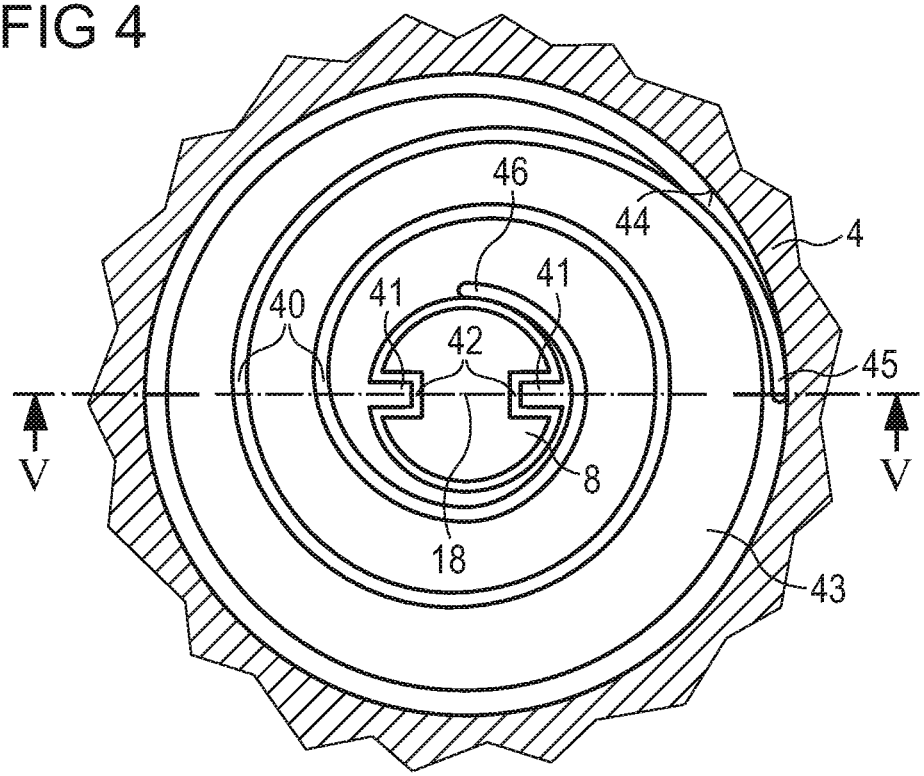

DRUG DELIVERY DEVICE

CROSS REFERENCE TO RELATED APPLICATIONS

The present application is a continuation of U.S. patent application Ser. No. 15/352,904, filed Nov. 16, 2016, which is a continuation of U.S. patent application Ser. No. 13/258,160, filed Dec. 6, 2011, now U.S. Pat. No. 9,526,840, which is a U.S. National Phase Application pursuant to 35 U.S.C. § 371 of International Application No. PCT/EP2010/054343 filed Mar. 31, 2010, which claims priority to European Patent Application No. 09004666.5 filed on Mar. 31, 2009 and U.S. Provisional Patent Application No. 61/169,868 filed on Apr. 16, 2009. The entire disclosure contents of these applications are herewith incorporated by reference into the present application.

FIELD OF INVENTION

The present invention relates to a drug delivery device, particularly to a portable pen-type drug injector.

BACKGROUND

Portable drug delivery devices are used for the administration of a medicinal fluid or drug. A drug injection device is especially useful in the shape of a pen. A dose of a drug is delivered by means of a drive mechanism using a piston driven by a piston rod. The device may be refillable, especially by means of exchangeable cartridges, which contain the drug to be injected and are inserted in the body of the injection pen. In this case the piston can be arranged within the cartridge, while the piston rod is a component of the drive mechanism. When an emptied cartridge is substituted with a new one, the drive mechanism has to be reset.

EP 1 923 083 A1 describes a drug delivery device in the shape of an injection pen having a drive mechanism, which allows to deliver a plurality of different prescribed doses.

WO 2008/074897 A1 describes a syringe device in the shape of a pen. It comprises a container for a drug and a piston for the delivery of the drug, further a housing having a helical thread, a dose dial sleeve having a helical thread engaged with the helical thread of the housing, a drive sleeve detachably connected to the dose dial sleeve and a clutch means located between the dose dial sleeve and the drive sleeve. When the dose dial sleeve and the drive sleeve are coupled via the clutch means, both are allowed to rotate with respect to the housing. When the dose dial sleeve and the drive sleeve are decoupled, rotation of the dose dial sleeve with respect to the housing is allowed whilst rotation of the drive sleeve with respect to the housing is not allowed, whereby axial movement of the drive sleeve is allowed so that a force is transferred in the longitudinal direction to a piston rod for drug delivery.

SUMMARY

It is an object of the present invention to disclose a drug delivery device comprising a mechanism with a means that facilitates a reset of the mechanism.

This object is achieved with the drug delivery device according to claim 1. Further aspects and variations of the invention derive from the depending claims.

The drug delivery device comprises a housing or body with a receptacle for a drug. The body contains a piston rod, which is provided for delivering the drug out of the receptacle. A mechanism in the body is used to drive the piston rod and comprises means for guiding the movement of the piston rod relatively to the body while delivering the drug. Further means are provided for releasing the piston rod from the means for guiding the movement, thus enabling a reset of the piston rod to a start position, especially after the receptacle has been emptied and is to be refilled, for example. The device is constructed in such a manner that a reset of the piston rod is facilitated.

The term "drug delivery device" according to the invention shall mean a device designed to dispense a dose of a medicinal product, preferably multiple selected doses, e.g. of insulin, growth hormones, low molecular weight heparins, and their analogues and/or derivatives etc. Said device may be of any shape, e.g. compact or pen-type. Dose delivery may be provided through a mechanical, electrical or electro-mechanical dosing mechanism or by a stored energy dosing mechanism, such as a spring, etc. Furthermore, said device may comprise a needle or may be needle-free. Preferably, the term "drug delivery device" shall mean a reusable multi-dose pen-type device having mechanical and manual dose selection and dose delivery mechanisms, which is designed for regular use by persons without formal medical training such as patients. Preferably, the drug delivery device is of the injector-type. Most preferably the drug delivery device is designed to deliver a fluid drug.

The term "piston rod" according to the invention shall mean a device driving a piston, which is used to expel a substance or fluid from the receptacle. The dimensions of the piston rod may comprise a longitudinal major extension or axis, which is sufficiently large to enable an axial translational movement corresponding to the travel of the piston.

An embodiment of the drug delivery device comprises a body having a proximal and a distal end, a receptacle provided for a drug or pharmaceutical fluid near the distal end of the body, a piston rod which is movable in an axial direction from the proximal end towards the distal end for drug delivery, and a drive mechanism for the advancement of the piston rod.

A reset mechanism is provided for resetting the piston rod to a start position at the proximal end when the receptacle is empty.

The receptacle can be provided to be filled by inserting a cartridge containing the drug and a piston, which is to be moved by the piston rod. A receptacle provided for a cartridge is refilled by removing an emptied cartridge, resetting the piston rod, and inserting a new cartridge.

The term "drug", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

In a further embodiment of the drug delivery device, the reset operation is merely generated by the weight of the piston rod. The reset operation is started by a release of the piston rod, so that the piston rod is free to move. If the device is then held with its proximal end pointing downwards, the gravitation makes the piston rod return to a start position at the proximal end. This movement may be accompanied with a rotation of the piston rod relatively to the body of the device and may especially be a helical movement generated by a screw thread of the piston rod.

The materials of the piston rod and further elements of the mechanism on which the piston rod slides during the reset operation are selected in view of making these components sufficiently smooth-running on one another, and the surfaces are given a finish that is most suitable to this purpose. If the device is held with its proximal end pointing down, the downward force exerted by the piston rod due to its weight suffices to generate a sliding movement of the piston rod back into the drive mechanism. A dedicated reset element is therefore not necessary.

In a further embodiment of the drug delivery device, a mechanism is provided, by which the doses to be administered can be preset. A mechanism of this kind may be constructed according to the following description, for example. The piston rod comprises a screw thread at the distal end and a further screw thread at the proximal end, the screw threads having different pitches and opposite senses of rotation. The first screw thread is provided for the generation of a helical movement of the advancing piston rod, during the delivery of a preset dose, by means of a piston rod nut, which is kept fixed relatively to the body. The further screw thread is provided for a threaded engagement with a drive sleeve of the drive mechanism. During the setting of a dose the piston rod is prevented from rotation and axial translation relatively to the body by the combined effect of the thread of the fixed piston rod nut and the thread of the drive sleeve, which moves helically around the piston rod without changing the position of the shape of the surface that faces the further screw thread of the piston rod. The thread of the drive sleeve therefore appears during the set operation as if it were fastened to the body, apart from the sliding movement on the surface of the piston rod.

When a reset operation is started, the piston rod nut is detached from the body. This may be effected by removing the empty cartridge, for example. The piston rod is now able to rotate relatively to the body like a screw into the drive sleeve, until a start position is attained. Furthermore, the piston rod nut is also allowed to rotate freely in order to compensate for a discrepancy between the actual helical movement of the piston rod and a helical movement that would be generated by the thread of the piston rod nut if it were still fixed relatively to the body. After the detachment of the piston rod nut a translational movement of the piston rod in the axial direction towards the proximal end is therefore possible independently of the pitch of the thread of the piston rod nut.

In a further embodiment of the drug delivery device, the mechanism is constructed in such a manner that to reset the piston rod it has to be rotated relatively to the body in a sense of rotation that is opposite to the sense of rotation of the piston rod during drug delivery. The means for guiding the movement of the piston rod are provided to generate a rotation of the piston rod relatively to the body while delivering the drug. A spring element is loaded by the rotation of the piston rod, while delivering the drug, in such a manner as to make the spring element tend to rotate in a sense of rotation that is opposite to the sense of rotation of the piston rod while delivering the drug. The spring element is engaged with the piston rod in such a manner that a rotation of the spring element generates a rotation of the piston rod of the same sense of rotation.

In a further embodiment comprising a spring element, a reset nut is provided for the reset operation. The reset nut is located coaxially around the piston rod, which passes through a central hole of the reset nut. The diameter of the hole is sufficient to permit a free movement of the piston rod through the reset nut. On the inner sidewall of the hole, there is at least one spline, which engages a groove of the piston rod. The groove is formed on the surface of the piston rod, irrespective of a screw thread of the piston rod, and extends at least mainly in axial direction. It may especially run straight along the piston rod, parallel to the axis of the piston rod. Instead, the groove may be wound helically around the piston rod. It may be favourable to have at least two splines, arranged at opposite locations of the circumference of the hole, and two corresponding grooves on the piston rod.

The reset nut carries a spring, which can be a spiral spring arranged in a plane perpendicular to the axis of the piston rod. The ends of the spring are fastened to the body and to the reset nut, respectively, in such a manner that the spring is loaded when the reset nut is turned in the rotational sense of the piston rod during the drug delivery operation. Because of the spline or splines and the corresponding groove or grooves and the fastening of the spring to the body, the reset nut is rotated by a helical movement of the piston rod without being moved in axial direction. The spring of the reset nut is held fixed to the same location of the inner surface of the body, while the reset nut is rotated by the rotation of the piston rod, irrespective of the translational movement of the piston rod. The groove or grooves of the piston rod may be wound helically around the piston rod in such a manner as to generate a suitable number of rotations of the reset nut in total, until the piston rod reaches its final position at the distal end. The number of rotations of the reset nut can thus be adapted to the properties of the spring, which does not reach its state of maximal tension or stress before the axial translation of the piston rod is completed. The loaded spring reverses the total rotation of the piston rod once the piston rod nut is detached, and the piston rod is driven to perform a helical movement into the drive mechanism.

BRIEF DESCRIPTION OF THE FIGURES

Further aspects and examples of the invention are described in conjunction with the appended figures.

FIG. 3 shows a partial cross-section of a further embodiment of an injection pen comprising a reset nut.

FIG. 4 shows an enlarged plane view of the arrangement of the reset nut, at the position indicated in FIG. 3.

DETAILED DESCRIPTION

Figure 1:
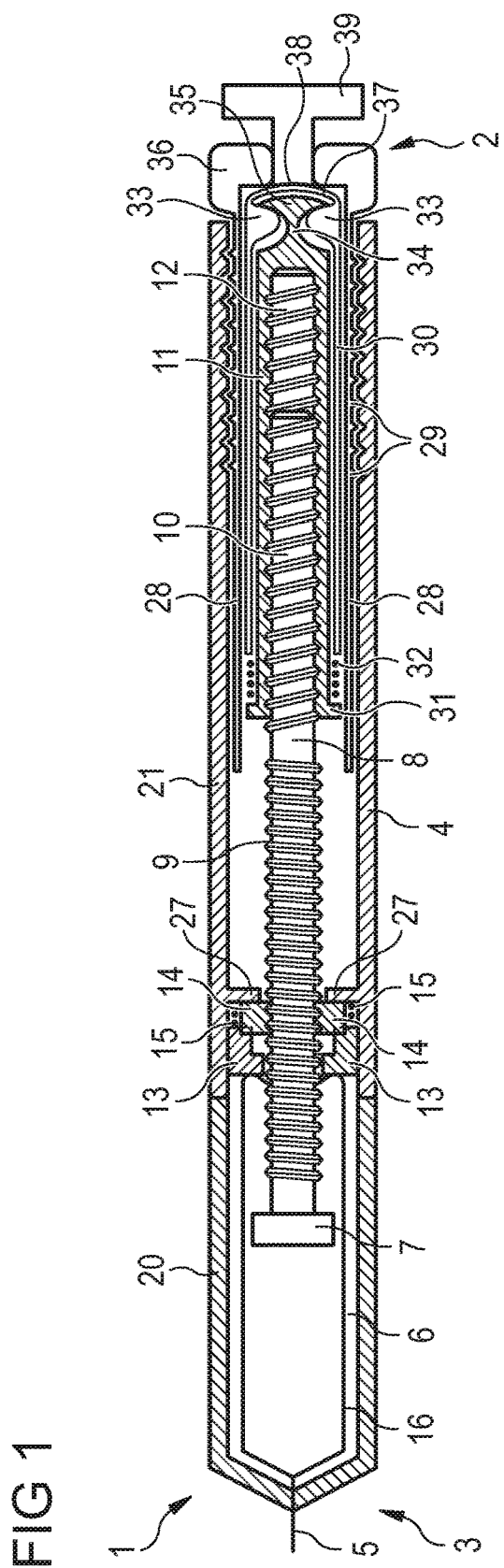
FIG. 1 shows a cross-section of an injection pen having a mechanism comprising a reset operation.

FIG. 1 shows a cross-section of an injection device 1 in the shape of a pen having a proximal end 2, a distal end 3 and a housing or body 4 carrying a needle 5 at the distal end 3. A receptacle 6 serving as a reservoir for a drug that is to be injected through the needle 5 is provided at the distal end 3 and can be refilled. The delivery of the drug is effected by means of a piston 7, which is moved by a piston rod 8 in the axial direction, along the longitudinal extension of the device, thus reducing the volume of the reservoir according to the doses to be administered. The receptacle 6 can be provided for the insertion of a cartridge 16 containing the drug. In this case, the piston 7 is moved in the cartridge 16 and the piston rod 8 moves through a hole in the bottom of the cartridge 16. At the distal end 3 the body 4 comprises a distal part 20, which can be taken off from a proximal part 21 of the body 4, so that the cartridge 16 can be removed and substituted with another one.

The piston rod 8 carries a screw thread 9 at its distal end and passes through a central hole of a piston rod nut 14, which has a thread of the same pitch on the inner wall of its central hole. The piston rod 8 and the piston rod nut 14 are interlocked by the screw thread 9 and can be rotated relatively to one another. Simultaneously with the rotation, the screw thread 9 generates an axial relative movement resulting in an overall helical relative movement. The piston rod 8 and the piston rod nut 14 thus form a pair of sliding elements. The friction between these elements is reduced if they are formed from low-friction synthetic materials.

A lock nut 13 is engaged with the piston rod nut 14 by means of a coupling device. A spring 15 is arranged between the lock nut 13 and a barrier rim 27 or transverse inner wall of the body 4. The coupling device can be realized, for instance, by a gear formed by surface structures of the nuts 13, 14. When the injection pen 1 is ready for use, the spring 15 is compressed by the cartridge 16 inserted in the receptacle 6, and the coupling device engages the nuts 13, 14. The compressed spring tends to shift the lock nut 13 towards the distal end 3 and thereby disengage the lock nut 13 and the piston rod nut 14.

Figure 2:
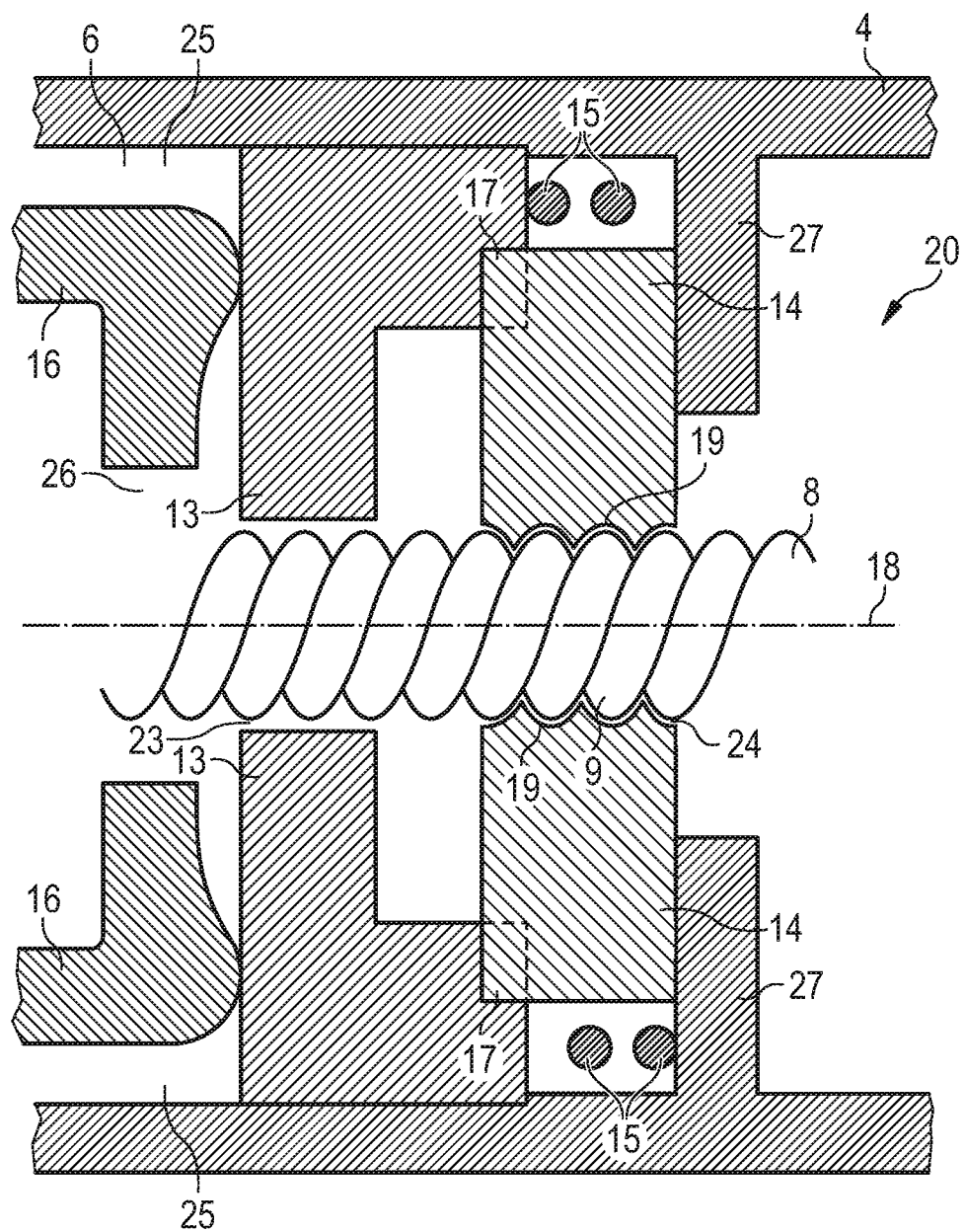
FIG. 2 shows an enlarged cross-section of a part of the mechanism that is involved in the reset operation.

FIG. 2 shows an enlarged view of the arrangement of the lock nut 13 and the piston rod nut 14. In the center of FIG. 2, a section of the piston rod 8 is shown. An imaginary central axis 18 is indicated by the broken line of alternating dots and dashes. The piston rod 8 goes through a hole 23 of the lock nut 13, a hole 24 of the piston rod nut 14 and a hole 26 in the bottom of the cartridge 16, which is inserted in the receptacle 6. The spring 15, which may be a helical spring, surrounds the piston rod 8 and is arranged between the lock nut 13 and the barrier rim 27, which can be an integral part of the body 4. The outermost surfaces of the spring 15 are in contact with the surfaces of the lock nut 13 and the barrier rim 27 facing the spring 15.

The coupling device 17 engaging the lock nut 13 and the piston rod nut 14 can be formed by a sequence of interlocking teeth or some other kind of gear, for example. This is indicated in FIG. 2 by the lock nut 13 partially intruding the outer margin of the piston rod nut 14 in the area of the coupling device 17. The lock nut 13 is engaged with the body 4, by means of protruding parts or recesses, for example, so that the lock nut 13 cannot rotate relatively to the body 4 around the axis 18 of the piston rod 8, but can axially move at least a small distance towards the distal end 3. In the embodiment shown in FIG. 2 this is effected by grooves 25 forming internal splines in the inner sidewall of the body 4, which guide external splines on the circumference of the lock nut 13. An axial movement of the lock nut 13 towards the distal end 3 is inhibited by the presence of the cartridge 16. An axial movement of the nuts 13, 14 in the direction towards the proximal end 2 can be inhibited by barrier rims 27, spikes or a partial transverse wall of the body 4, for example, fixed at the inner surface of the body 4 or forming an integral part of the body 4 on the side of the nuts 13, 14 facing away from the piston 7.

The hole 24 of the piston rod nut 14 is supplied with a thread 19 having the same pitch as the screw thread 9 of the piston rod 8. Thus, the thread 19 of the piston rod nut 14 is the female thread counterpart of the male screw thread of the piston rod 8. If the nuts are engaged by the coupling device 17 as shown in FIG. 2, a relative rotation of the lock nut 13 and the piston rod nut 14 is inhibited, and the piston rod nut 14 cannot rotate relatively to the body 4 around the piston rod 8 because the lock nut 13 is rotationally fixed by the protruding parts, recesses or grooves 25.

If the cartridge 16 is removed and the spring 15 is released, the coupling device 17 is no longer interlocked, and the lock nut 13 and the piston rod nut 14 are disengaged. This means that the piston rod nut 14 can freely rotate around the piston rod 8, and the piston rod 8 is able to perform a translational movement along its axis 18 irrespective of a rotation around its axis 18. This is, because the piston rod nut 14 will freely rotate and compensate for a discrepancy between the actual translational movement of the piston rod 8 and a translational component of a helical movement of the piston rod 8 that would be generated by the threads 9, 19 when the piston rod nut 14 is rotationally fixed.

The operations of setting and delivering a dose will now be described in conjunction with FIG. 1, which shows, by way of example, an embodiment that comprises means for setting a dose, including the piston rod 8 and further components arranged in the proximal part 21 of the body 4. The piston rod 8 is provided with a further screw thread 10 at its proximal end. A drive sleeve 11 having an inner thread 12 of the same pitch is interlocked with the further screw thread 10 of the piston rod 8. A dial sleeve 28 having a helical thread engaged with a helical thread 29 of the body 4 and having the same pitch as the further screw thread 10 of the piston rod 8 is arranged around the drive sleeve 11 and can be rotated by the user by means of a dial grip 36, which surpasses the proximal end 2 of the body 4, for example. A clutch 30 of essentially cylindrical shape is arranged between the drive sleeve 11 and the dial sleeve 28.

The drive sleeve 11 is provided with a kind of rim or collar 31 at its distal end. A spring 32 is arranged between the collar 31 and the clutch 30 and tends to press the clutch 30 against the inner surface of a proximal end face of the dial sleeve 28, where a gear 37 or similar surface structure is provided to inhibit, when engaged, a relative rotation of the clutch 30 with respect to the dial sleeve 28. A translational movement of the drive sleeve 11 relatively to the clutch 30 can preferably be limited by hooks 35 of the drive sleeve 11, which are stopped by the proximal end of the clutch 30. A relative rotation of the clutch around the drive sleeve 11 is permanently inhibited, for instance, by clutch leads 33 engaging a gear 34 at the proximal end of the drive sleeve 11 in such a manner that the clutch 30 can be shifted a short distance relatively to the drive sleeve 11 towards the distal end of the drive sleeve 11 against the force of the clutch spring 32. This shift can be effected by means of an operation button 39 arranged at the proximal end 2 of the body 4 in contact with an end face 38 of the clutch. If the operation button 39 is pressed, the clutch 30 is shifted towards the distal end 3 and disengaged from the gear 37 of the dial sleeve 28, so that a relative rotation between the clutch 30 and the dial sleeve 28 is made possible.

During the set operation to select a dose of the drug to be delivered, the operation button 39 is not pressed and the dial sleeve 28 and the clutch 30 are rotationally coupled by the gear 37. By rotating the dial grip 36, the dial sleeve 28 is moved out of the body 4 in a helical movement generated by the thread 29. Because of the rotational coupling, the dial sleeve 28, the clutch 30 and the drive sleeve 11, forming a dial assembly, always rotate by the same angle. Because the threads of the drive sleeve 11 and the dial sleeve 28 have the same pitch, the position of the shape of the surface that faces the further screw thread 10 of the piston rod 8 does not change during the helical movement of the dial assembly. The piston rod 8 thus always sees the same spatial position of the inner thread of the drive sleeve 11, as if this thread were an integral part of the body 4. The piston rod nut 14 is fixed during the set operation, so that its thread 19 also appears as if it were an integral part of the body 4. Since the two threads 9, 10 of the piston rod 8 have different pitches, and also different senses of rotation, the different helical movements corresponding to the different pitches cannot be performed simultaneously by the stiff piston rod 8, which is therefore fixed relative to the body 4 and neither moves in axial direction nor rotates. The rotation of the dial assembly takes therefore place without changing the relative axial position of the dial sleeve 28 and the drive sleeve 11, so that the clutch 30 remains engaged with the dial sleeve 28 by means of the gear 37.

After the desired dose has been set, it may be delivered by pressing the operation button 39 and moving the piston rod 8 towards the distal end 3. The operation button 39 extends through the dial grip 36 and is in contact with a proximal end face 38 or other extreme end part of the clutch 30. When the operation button 39 is pressed, clutch 30 is axially shifted towards the distal end 3 of the device with respect to the dial sleeve 28, thereby decoupling the clutch 30 from the dial sleeve 28. However, the clutch 30 remains keyed in rotation to the drive sleeve 11. Therefore the decoupling of the clutch 30 results in a decoupling of the dial sleeve 28 and the drive sleeve 11. The dial sleeve 28 is free to rotate in a helical movement according to the thread 29, thus moving back into the body 4 to its original position. The clutch 30 is being kept from rotation either by the operation button 39 directly, for instance, or by some other means not shown in FIG. 1, which may be arranged between an outer structure of the clutch 30 and axial grooves in the body 4, for instance, in order to guide the movement of the clutch, allowing an axial translation but inhibiting a rotation. The drive sleeve 11, which cannot be rotated relatively to the clutch 30, is therefore not wound around the piston rod 8 as during the set operation, but shifts the piston rod 8 towards the distal end 3. The piston rod 8 performs a helical movement with respect to the body 4 through the piston rod nut 14. Because of the different senses of rotation of the screw threads 9, 10 of the piston rod 8, the drive sleeve 11 is moved towards the piston rod nut 14, and the axial displacement of the drive sleeve 11 exceeds the displacement of the piston 7, which is defined by the axial translation of the piston rod 8 relatively to the body 4. The different pitches of the screw threads 9, 10 of the piston rod 8 define the relation between the distance that the dial assembly is axially moved per unit dose during the set operation and the distance that the piston 7 is moved during the delivery of one unit dose, and the pitches can be adjusted to provide a desired transmission for easy use. The pitch of the thread of the drive sleeve 11, corresponding to the further screw thread 10 of the piston rod 8, is preferably larger than the pitch of the thread of the piston rod nut 14.

When the final dose has been dispensed, the cartridge 16 is empty and may be removed. To this end, the distal part 20 of the body is taken off together with the cartridge 16, and the lock nut 13 is released. The spring 15 moves the lock nut 13 away from the piston rod nut 14, so that the nuts 13, 14 are no longer engaged by the coupling device 17. Then the piston rod nut 14 can rotate relatively to the body 4 and is ready for the reset operation.

During reset, the piston rod 8 is screwed into the drive sleeve 11 towards the proximal end 2. To this purpose it may suffice to hold the injection device with its proximal end 2 downwards and have the piston rod 8 rotate into the drive sleeve 11, following the gravitation of its own weight. In order to achieve this, the materials of the sliding elements are selected to be sufficiently smooth-running.

The friction between rough planar surfaces of two bodies that are in contact and move relatively to one another, so that the surfaces slide on one another, generates a force FR of a retarding effect directed within the plane of the surfaces, thus decreasing the velocity of the relative movement. At a certain specified relative speed of the bodies, the absolute value of the frictional force FR can generally be regarded as being proportional to the absolute value of a force FN perpendicular to the plane of the surfaces, by which the bodies are pressed on one another. The quotient of the absolute value of the frictional force FR and the absolute value of the perpendicular force FN is called coefficient μ of sliding friction, so that the equality FR=μ(vr)×FN is supposed for any specified relative velocity vr of the bodies.

If the mechanical elements are made of synthetic or plastic material, a value of the coefficient μ of sliding friction of typically 0.25 or less at a relative velocity of the sliding surfaces of 2 mm per second can be obtained. The piston rod 8 may be a liquid crystalline polymer and the piston rod nut 14 and the drive sleeve 11 polyoxymethylene, for example. A comparable value of μ can be obtained for the sliding movement of the piston rod nut 14 on a surface or barrier rim 27 of a body 4 made of synthetic or plastic material.

The properties of the materials can also be specified by the roughness of their surfaces. The roughness can be measured by the deviation of the actual rough surface from a smooth reference surface. A characteristic parameter of the roughness is the average of the absolute value of the distance between a point of the actual surface and the corresponding point of the reference surface, called centre line average. The materials of the piston rod 8, the piston rod nut 14 and the drive sleeve 11 are preferably selected to have a centre line average of less than 1.6 μm.

A further parameter that is relevant with respect to the ease of the sliding motion of the piston rod 8 through the threads is the pitch of the threads. A pitch of a screw thread can be specified, depending on the diameter of the screw, by the angle between the axis of the screw and the tangents of the helix formed by the thread. The reset operation is promoted if the angle between the axis 18 of the piston rod 8 and the tangents of the helices of the threads 9, 10 is as large as feasible. This angle can be made at least 25° for the thread of the piston rod nut 14 and at least 40° for the thread of the drive sleeve 11. Larger values may be favourable to the reset operation, but upper limits of the angles are imposed by the shape and dimensions of the device.

In a further embodiment of the injection device according to FIG. 3, the reset operation is effected by a reset element. In this embodiment the mechanism is constructed in such a manner that to reset the piston rod 8 it has to be rotated relatively to the body 4 in a sense of rotation that is opposite to the sense of rotation of the piston rod 8 during drug delivery. Although a mechanism of this kind may be constructed without the nuts 13, 14 and spring 15 described above, the distal part of the mechanism of the embodiment of FIG. 3 is represented in a fashion to be comparable to the mechanism of the embodiment according to FIGS. 1 and 2 for easy reference.

The mechanism of the embodiment according to FIG. 3 comprises a reset nut 43 having a central hole with a sidewall carrying a protruding structure, which can be at least one spline 41 or spike, for example, as shown in FIG. 4. The piston rod 8 goes through the central hole of the reset nut 43, which is arranged transversely to the axis 18 of the piston rod 8. The protruding structure of the reset nut 43 is engaged in at least one groove 42 of the piston rod 8, which runs along the surface of the piston rod 8 and intersects the thread without affecting the helical movement generated by the thread. The groove 42 can run along a straight line parallel to the axis 18 or be wound helically around the piston rod 8. The engagement between the piston rod 8 and the reset nut 43 generates a rotation of the reset nut 43 according to the rotation of the piston rod 8. The piston rod 8 can move axially through the reset nut 43, owing to the longitudinally extending groove 42, while the reset nut 43 is only rotated and can be held in its axial position.

A spring 40, which is preferably a spiral spring, is attached to the reset nut 43 and fastened to an inner surface 44 of the body 4 or another element that is relatively fixed to the body 4. The positions of the fastening 45 of the spring 40 to the body 4 and of the fastening 46 of the spring 40 to the reset nut 43 as well as the arrangement of the spiral spring 40 on a surface of the reset nut 43 can be seen in cross-section in FIG. 3, in a plan view in FIG. 4, and in an enlarged cross-section in FIG. 5.

The spiral spring 40 is arranged in such a manner that it is loaded when the reset nut 43 is turned in the rotational sense of the piston rod 8 during the drug delivery operation. Because of the spline 41 or splines 41 and the corresponding groove 42 or grooves 42 and the fastening of the spring 40 to the body 4, the reset nut 43 is rotated by the helical movement of the piston rod 8 without being moved in axial direction. The spring 40 and with it the reset nut 43 are thus always held at their axial position with respect to the body 4. The total number of rotations performed by the reset nut 43 until the reservoir is empty can be adjusted by the straight or helical shape of the groove 42 or grooves 42. The spring 40 is repeatedly loaded to increase its tension or stress, but does not reach its state of maximal tension or stress before the axial translation of the piston rod 8 is completed.

When the reset operation is initiated by releasing the piston rod 8, the spring 40 reverses the overall rotation of the piston rod 8, and the piston rod 8 is driven like a screw back into the drive mechanism. While the rotation is generated by the spring 40, the helical movement can be generated by a screw thread of the piston rod 8 sliding in the thread of a fixed piston rod nut 14, for example, or, if the piston rod nut is released or if no piston rod nut is used, sliding in a thread of another element of the mechanism.

Figure 5:
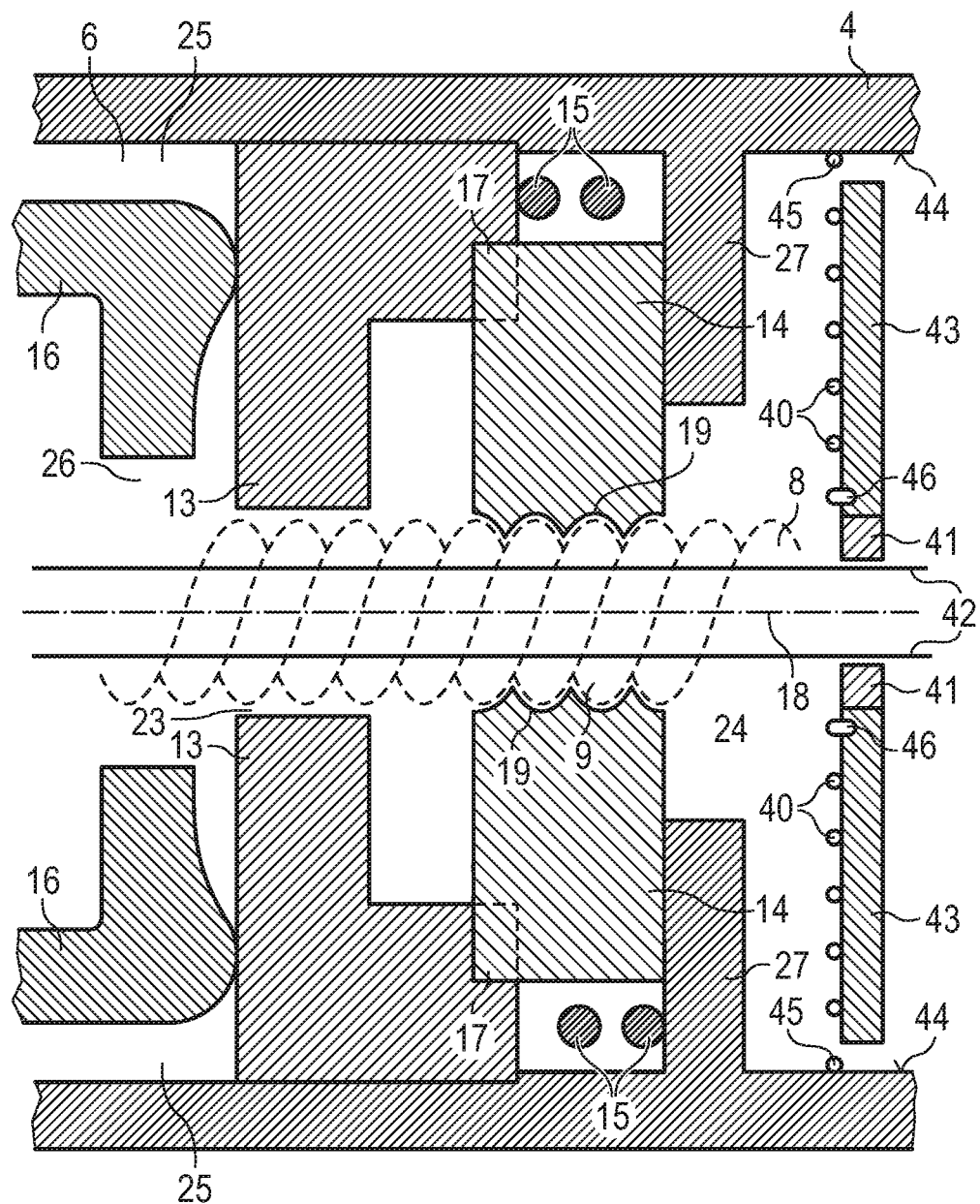
FIG. 5 shows an enlarged cross-section of a part of the mechanism that is involved in the reset operation.

FIG. 5 shows a variant of the embodiment according to FIG. 3, which comprises at least two spiral springs 40 arranged at the reset nut 43. Each spiral spring 40 is fastened to the body 4 and to the reset nut 43 by fastenings 45, 46. The spiral springs 40 can be arranged so as to form a double or multiple line or band winding along a spiral.

Features of the described embodiments can be combined. In particular, the reset nut can be provided in a mechanism comprising sliding elements formed from smooth-running materials. The pitch of the screw thread that is responsible for the helical motion of the piston rod 8 during the reset can be made large enough to facilitate the back-winding of the reset nut 43 and spring 40. The angle between the axis 18 of the piston rod 8 and the tangents of the helix formed by said screw thread can be more than 40° to this purpose.

The invention claimed is:

1. A drug delivery device comprising:
a body having a receptacle for a drug;
a piston rod in the body, the piston rod being movable relatively to the body and being provided for expelling the drug out of the receptacle, wherein the piston rod comprises an axis and a screw thread;
a mechanism provided to drive the piston rod while delivering the drug, the piston rod having a start position with respect to the mechanism prior to delivery of a first portion of the drug;
a device for guiding movement of the piston rod relatively to the body while delivering the drug, the device comprising a reset nut located coaxially around the piston rod, the piston rod passing through a central hole of the reset nut, wherein at least one spline is on an inner sidewall of the hole, the at least one spline engaging a groove of the piston rod, wherein the groove of the piston rod runs straight along the piston rod and parallel to the axis of the piston rod;
a device for releasing the piston rod from the device for guiding the movement, the device for releasing being provided to enable a reset of the piston rod to the start position; and
a drive sleeve having a thread corresponding to the screw thread of the piston rod and engaging the screw thread of the piston rod,
wherein the reset of the piston rod to the start position comprises a helical movement of the piston rod relative to the drive sleeve according to the screw thread of the piston rod, and
wherein the reset is merely generated by a weight of the piston rod.

2. The drug delivery device according to claim 1, wherein the groove of the piston rod is formed on a surface of the piston rod, irrespective of the screw thread of the piston rod.

3. The drug delivery device according to claim 1, wherein at least two splines are on the inner sidewall of the hole, the at least two splines arranged at opposite locations of a circumference of the hole, and wherein the piston rod comprises at least two corresponding grooves.

4. The drug delivery device according to claim 1, wherein the reset nut carries a spring.

5. The drug delivery device according to claim 1, wherein the drive sleeve is formed from synthetic or plastic materials that have a coefficient of sliding friction of at most 0.25 at a relative velocity of sliding surfaces of 2 mm per second.

6. The drug delivery device according to claim 1, wherein the reset nut is formed from synthetic or plastic materials that have a coefficient of sliding friction of at most 0.25 at a relative velocity of sliding surfaces of 2 mm per second.

7. The drug delivery device according to claim 1, wherein the body comprises a proximal end and a distal end, and wherein the receptacle for the drug is provided near the distal end of the body.

8. The drug delivery device according to claim 1, wherein the reset is started by a release of the piston rod, so that the piston rod is free to move.

* * * * *

UNITED STATES PATENT AND TRADEMARK OFFICE
CERTIFICATE OF CORRECTION

PATENT NO. : 10,398,845 B2  
APPLICATION NO. : 15/805924  
DATED : September 3, 2019  
INVENTOR(S) : Michael Harris et al.

Page 1 of 1

It is certified that error appears in the above-identified patent and that said Letters Patent is hereby corrected as shown below:

In the Specification

Column 1, Line 14, under "CROSS REFERENCE TO RELATED APPLICATIONS", delete "61/169,868" and insert -- 61/169,858 --.

Signed and Sealed this  
Fourth Day of February, 2020

Andrei Iancu  
*Director of the United States Patent and Trademark Office*